United States Patent
Onodera et al.

(10) Patent No.: US 11,273,109 B2
(45) Date of Patent: Mar. 15, 2022

(54) COSMETIC INK, INK JET PRINTING INK AND INK CARTRIDGE CONTAINING COSMETIC INK, COSMETIC SHEET, AND METHOD FOR PRODUCING COSMETIC SHEET

(71) Applicant: Panasonic Intellectual Property Management Co., Ltd., Osaka (JP)

(72) Inventors: Mari Onodera, Osaka (JP); Masayo Shinoda, Tokyo (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 16/711,792

(22) Filed: Dec. 12, 2019

(65) Prior Publication Data

US 2020/0121573 A1   Apr. 23, 2020

Related U.S. Application Data (63) Continuation of application No. PCT/JP2018/021636, filed on Jun. 6, 2018.

(30) Foreign Application Priority Data

Jul. 3, 2017 (JP) .............................. JP2017-130382
Dec. 21, 2017 (JP) .............................. JP2017-245242

(51) Int. Cl.
| | | |
|---|---|---|
| *A61K 8/81* | (2006.01) | |
| *A61Q 1/02* | (2006.01) | |
| *A61K 8/34* | (2006.01) | |
| *A61K 8/02* | (2006.01) | |
| *A61K 8/60* | (2006.01) | |
| *A61K 8/73* | (2006.01) | |

(52) U.S. Cl.
CPC .......... *A61K 8/345* (2013.01); *A61K 8/0204* (2013.01); *A61K 8/60* (2013.01); *A61K 8/73* (2013.01); *A61K 8/8152* (2013.01); *A61Q 1/02* (2013.01); *A61K 2800/412* (2013.01); *A61K 2800/43* (2013.01)

(58) Field of Classification Search
None
See application file for complete search history.

(56) References Cited

U.S. PATENT DOCUMENTS

| | | | | |
|---|---|---|---|---|
| 6,933,048 | B2* | 8/2005 | Phillips ................. | C09C 1/0078 428/403 |
| 9,125,839 | B2* | 9/2015 | Kachi .................... | A61Q 19/00 |
| 2002/0007768 | A1 | 1/2002 | Yoshimura et al. | |
| 2015/0265030 | A1 | 9/2015 | Kusukame et al. | |
| 2016/0130453 | A1 | 5/2016 | Eguchi et al. | |
| 2016/0316886 | A1* | 11/2016 | Samain .................. | A45D 33/00 |
| 2017/0073535 | A1* | 3/2017 | Kusukame ........... | C09D 11/107 |

FOREIGN PATENT DOCUMENTS

| | | |
|---|---|---|
| EP | 2862907 A1 | 4/2015 |
| EP | 3144356 A1 | 3/2017 |
| JP | 2002-105373 | 4/2002 |
| JP | 2005-505505 | 2/2005 |
| JP | 2010-256470 | 11/2010 |
| JP | 2015-013990 | 1/2015 |
| JP | 2015-193604 | 11/2015 |
| JP | 2016-216675 | 12/2016 |
| JP | 2017-057261 | 3/2017 |
| WO | 2002/094423 | 11/2002 |
| WO | 2015/191823 | 12/2015 |

OTHER PUBLICATIONS

International Search Report of PCT application No. PCT/JP2018/021636 dated Jul. 31, 2018.
The Extended European Search Report dated Jun. 24, 2020 for the related European Patent Application No. 18827485.6.

* cited by examiner

*Primary Examiner* — Celeste A Roney
(74) *Attorney, Agent, or Firm* — Greenblum & Bernstein, P.L.C.

(57) ABSTRACT

There are provided a cosmetic ink that can be applied to a light-transmitting sheet to form an image with high hiding power and a method for producing a cosmetic sheet using the cosmetic ink. There are also provided a cosmetic ink with good drying characteristics and a method for producing a cosmetic sheet using the cosmetic ink. Such a cosmetic ink contains a reflecting agent, a higher alcohol having 3 or more carbon atoms, purified water, and a binder. The cosmetic sheet includes a sheet and a film of a solidified product of the cosmetic ink formed on the sheet.

21 Claims, 5 Drawing Sheets

COMPARATIVE EXAMPLE A

EXAMPLE A

COMPARATIVE EXAMPLE A

FIG. 4B

EXAMPLE A

COSMETIC INK, INK JET PRINTING INK AND INK CARTRIDGE CONTAINING COSMETIC INK, COSMETIC SHEET, AND METHOD FOR PRODUCING COSMETIC SHEET

BACKGROUND

1. Technical Field

The present disclosure relates to a cosmetic ink with high hiding power or good drying characteristics, an ink jet printing ink and an ink cartridge each containing the cosmetic ink, a cosmetic sheet, and a method for producing the cosmetic sheet.

2. Description of the Related Art

A known water-based ink contains a coloring material and a wetting agent, such as glycerin. Known typical water-based inks are supposed to be applied to highly absorbent bases, such as paper, and may achieve an unsatisfactory print density or scratch resistance when applied to low absorbent bases.

To address such problems, for example, Japanese Unexamined Patent Application Publication No. 2015-13990 (Patent Literature 1) discloses a pigment-containing ink jet ink containing insolubility polymer particles, a pigment, an organic solvent, and water.

A cosmetic containing a polyoxyethylene sorbitol fatty acid ester, polyoxyethylene hydrogenated castor oil, solid oil, a higher alcohol, and purified water is proposed as a cosmetic directly applied to the skin (Japanese Unexamined Patent Application Publication No. 2010-256470 (Patent Literature 2)).

SUMMARY

In recent years, the present inventors have studied on a cosmetic sheet to be put on the skin, wherein the cosmetic sheet is formed by printing on a very thin, visible-light-transmitting substrate. To produce such a cosmetic sheet, a known ink to be applied to paper, for example, an ink jet ink described in Patent Literature 1 may be used as a cosmetic to be applied to the sheet. However, light passes easily through a coating film of a known ink jet ink, such as one described in Patent Literature 1, applied to a visible-light-transmitting substrate.

A known cosmetic, for example, a cosmetic described in Patent Literature 2 may be directly applied to a substrate. A simple application of a known cosmetic, however, requires a long drying time.

In one general aspect, the techniques disclosed here feature a cosmetic ink containing (A) a reflecting agent, (B) a higher alcohol having 3 or more carbon atoms, (C) purified water, and (F) a binder.

In one aspect of a cosmetic ink according to the present disclosure, an image with high hiding power can be formed on a light-transmitting sheet. A cosmetic ink according to another aspect of the present disclosure has good drying characteristics after printing.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION (Underlying Knowledge Forming Basis of the Present Disclosure)

In recent years, the present inventors have studied on a cosmetic sheet to be put on the skin, wherein the cosmetic sheet is formed by printing on a very thin, visible-light-transmitting substrate. An ink jet ink described in Patent Literature 1 may be used to produce such a cosmetic sheet. However, light passes easily through a coating film of an ink jet ink described in Patent Literature 1 applied to a visible-light-transmitting substrate, and the color of a component (for example, skin) on which a cosmetic sheet is placed may be seen through the cosmetic sheet. Thus, it is difficult to provide a cosmetic sheet with high hiding power for chloasma. Furthermore, an ink jet ink described in Patent Literature 1 applied to a low absorbent substrate requires a long drying time.

A known cosmetic, for example, a cosmetic described in Patent Literature 2 may be directly applied to a substrate. A simple application of a known cosmetic, however, requires a long drying time, and the coating film has low scratch resistance. Furthermore, known cosmetics are difficult to apply with various printers and are rarely used to consistently produce cosmetic sheets with high hiding power.

Embodiments of the present disclosure are provided in view of such situations. An embodiment of the present disclosure provides a cosmetic ink that can be applied to a light-transmitting sheet to form an image with high hiding power and a method for producing a cosmetic sheet using the cosmetic ink. The present disclosure also provides a cosmetic ink with good drying characteristics and a method for producing a cosmetic sheet using the cosmetic ink.

1. Cosmetic Ink

A cosmetic ink according to the present disclosure is used to produce a cosmetic sheet. A cosmetic sheet formed from the ink can be put on, for example, the skin to color or beautify the skin. The cosmetic ink can be used not only in cosmetic applications, such as makeup, but also in skincare applications, such as a sunscreen, medical applications, and even industrial applications, such as decoration on plastic films. A cosmetic ink according to the present disclosure can be used in two embodiments depending on its composition. The two embodiments are described below.

1-1. First Embodiment

A cosmetic ink according to a first embodiment of the present disclosure contains (A) a reflecting agent, (B) a higher alcohol having 3 or more carbon atoms, (C) purified water, and (F) a binder. As described above, a printed material made from an ink used to produce a cosmetic sheet desirably has low optical transparency (high hiding power). Printed materials made from known typical ink jet inks, however, have high optical transparency. Thus, known typical ink jet inks are rarely used to produce printed materials with high hiding power. Furthermore, known typical cosmetics are difficult to apply with various printers and are rarely used to consistently produce cosmetic sheets including a film with high hiding power.

The cosmetic ink according to the present embodiment contains the (A) reflecting agent. The (A) reflecting agent in the cosmetic ink scatters or reflects light. Thus, the resulting printed material has a very low visible light transmittance and can be used, for example, in a cosmetic sheet that can sufficiently hide chloasma.

In addition to these components, the cosmetic ink according to the present embodiment may contain (E) a coloring material, a film forming agent, and various additive agents, if necessary. The components of the cosmetic ink according to the present embodiment are described in detail below.

<(A) Reflecting Agent>

The (A) reflecting agent in the cosmetic ink according to the present embodiment is composed of particles that scatter or reflect ultraviolet light and visible light (for example, light with a wavelength in the range of 200 to 780 nm) and may be any agent that can increase the hiding power of a printed material (an image formed)

The (A) reflecting agent preferably does not irritate the skin. Examples of the (A) reflecting agent include white pigments, such as titanium oxide, zinc oxide, cerium oxide, and barium sulfate; white extender powders, such as talc, muscovite, phlogopite, lepidolite, biotite, synthetic mica, sericite, synthetic sericite, kaolin, silicon carbide, bentonite, smectite, silicic anhydride, aluminum oxide, magnesium oxide, zirconium oxide, antimony oxide, diatomaceous earth, aluminum silicate, aluminum magnesium metasilicate, calcium silicate, barium silicate, magnesium silicate, calcium carbonate, magnesium carbonate, hydroxyapatite, and boron nitride; photoluminescent powders, such as calcium aluminum borosilicate, titanium dioxide coated mica, titanium dioxide coated glass powders, titanium dioxide coated bismuth oxychloride, titanium dioxide coated mica, titanium dioxide coated talc, iron oxide coated mica, iron oxide coated mica titanium, iron oxide coated glass powders, Prussian blue treated mica titanium, carmine treated mica titanium, bismuth oxychloride, argentine, poly(ethylene terephthalate)-aluminum-epoxy layered powders, and poly(ethylene terephthalate)-polyolefin laminated film powders; organic low-molecular-weight powders, such as N-acyl lysine; natural organic powders, such as silk powders and cellulose powders; metal powders, such as aluminum powders, gold powders, and silver powders; and composite powders, such as fine titanium oxide coated mica titanium, fine zinc oxide coated mica titanium, barium sulfate coated mica titanium, titanium-oxide-containing silicon dioxide, and zinc-oxide-containing silicon dioxide. The cosmetic ink may contain one or two or more of the (A) reflecting agents. Among these, preferred are titanium oxide, zinc oxide, cerium oxide, aluminum oxide, and magnesium oxide, and particularly preferred are titanium oxide, zinc oxide, and cerium oxide, in terms of ease with which a cosmetic sheet with high hiding power can be produced.

The (A) reflecting agent may have any shape, for example, spherical, plate-like, or acicular. The (A) reflecting agent preferably has an average particle size in the range of 125 nm to 2 µm. At an average particle size of 125 nm or more, a printed material produced tends to have increased hiding power, and a cosmetic sheet that hides, for example, chloasma can be easily produced. At an average particle size of 2 µm or less, the cosmetic ink can be applied with various printers (for example, ink jet apparatuses). The average particle size is the median (D50) of the integrated value of the particle size distribution measured by a laser diffraction method. The (A) reflecting agent more preferably has an average particle size (D50) in the range of 125 to 1000 nm. Still more preferably, the average particle size (D50) ranges from 125 to 1000 nm, and the 90% value (D90) of the integrated value of the particle size distribution is 3000 nm or less.

The amount of the (A) reflecting agent preferably ranges from 10 to 30 parts by mass per 100 parts by mass of the cosmetic ink. 10 parts or more by mass of the (A) reflecting agent tends to increase the hiding power of the coating film. 30 parts or less by mass of the (A) reflecting agent does not excessively increase the viscosity of the cosmetic ink, thus making application with various printers easier.

<(B) Higher Alcohol>

The higher alcohol in the cosmetic ink according to the present embodiment may be any higher alcohol that has 3 or more carbon atoms and that is compatible with the (C) purified water. The (B) higher alcohol functions as a solvent for the cosmetic ink. After the cosmetic ink is applied to a substrate, the (B) higher alcohol may be absorbed by the substrate or may be volatilize.

The (B) higher alcohol preferably has 3 to 5, more preferably 3 or 4, carbon atoms. The (B) higher alcohol having such a number of carbon atoms is easily compatible with the (C) purified water.

The (B) higher alcohol preferably contains a trivalent alcohol. The (B) higher alcohol containing a trivalent alcohol potentially prevents the (B) higher alcohol or the (C) purified water from volatilizing excessively within various printers. Consequently, the cosmetic ink can be stably applied with the printers. In this case, the cosmetic ink has a constant viscosity and can stably form desired images.

The trivalent alcohol may be any trivalent alcohol that does not irritate the skin and is preferably glycerin. Glycerin is biologically safe. Furthermore, glycerin in the cosmetic ink tends to suppress aggregation of the (A) reflecting agent or (E) a coloring material described later and potentially prevents an increase in viscosity of the cosmetic ink during long-term storage.

The (B) higher alcohol may contain a divalent alcohol or a monovalent alcohol. Examples of the divalent alcohol include diethylene glycol, propylene glycol, 1,3-propanediol, butylene glycol, and hexanediol. Examples of the monovalent alcohol include propanol, isopropanol, and butyl alcohol. Among these, a divalent alcohol, particularly propylene glycol, is preferred. Divalent alcohols have lower viscosity than the (C) purified water and trivalent alcohols and have low surface tension. Thus, a divalent alcohol in the cosmetic ink improves the wettability of the cosmetic ink to a substrate and potentially prevents unevenness of an image produced.

The total amount of the (B) higher alcohol is preferably 20 parts or less by mass, more preferably 10 to 20 parts by mass, per 100 parts by mass of the cosmetic ink. An excessively large amount of the (B) higher alcohol tends to result in aggregation of the (A) reflecting agent. 20 parts or less by mass of the (B) higher alcohol potentially prevents aggregation of the (A) reflecting agent and enables the cosmetic ink to be stably ejected from various printers.

The amount of trivalent alcohol per 100 parts by mass of the cosmetic ink is determined according to the method of applying the cosmetic ink. For example, for the cosmetic ink to be applied with an ink jet apparatus, the amount of trivalent alcohol is preferably 20 parts or less by mass, more preferably 10 to 20 parts by mass. When the amount of trivalent alcohol is in such a range, the (B) higher alcohol or the (C) purified water in the cosmetic ink has appropriately controlled volatility, and the cosmetic ink can be stably ejected from an ink jet apparatus.

The amount of divalent alcohol per 100 parts by mass of the cosmetic ink is also determined according to the method of applying the cosmetic ink. For example, for the cosmetic ink to be applied with an ink jet apparatus, the amount of divalent alcohol is preferably 20 parts or less by mass, more preferably 10 to 20 parts by mass. The cosmetic ink containing such an amount of divalent alcohol can easily have a viscosity in a desired range.

<(C) Purified Water>

The cosmetic ink according to the present embodiment contains the (C) purified water. The (C) purified water also functions as a solvent for the cosmetic ink and may be absorbed by a substrate or volatilize after the cosmetic ink is applied to the substrate.

The (C) purified water may be any purified water generally used for cosmetics and may be water purified by various methods such as distillation and ion exchange. For example, the (C) purified water may be hot spring water, deep water, or steam-distilled water of plants.

The amount of the (C) purified water is preferably 10 parts or more by mass, more preferably 20 parts or more by mass, per 100 parts by mass of the cosmetic ink.

<(F) Binder>

The cosmetic ink according to the present embodiment contains the (F) binder. The (F) binder is a compound that binds the (A) reflecting agent or the (E) coloring material described later to a substrate. The term "binder", as used herein, refers to a particulate resin insoluble in the (B) higher alcohol and the (C) purified water. The cosmetic ink may contain one or two or more of the (F) binders.

Examples of the (F) binder include particles composed of (meth)acrylic resins, such as alkyl (meth)acrylate polymers, styrene-(meth)acrylate copolymers, alkyl (meth)acrylate-vinyl acetate copolymers, (meth)acrylic acid-alkyl (meth) acrylate copolymers, and alkyl (meth)acrylate dimethicone polymers; vinyl acetate polymers; and vinylpyrrolidone-styrene copolymers. The term "(meth)acryl", as used herein, refers to acryl, methacryl, and a combination of acryl and methacryl.

Among these, the (F) binder is preferably composed of particles of a (meth)acrylic resin (hereinafter also referred to simply as "acrylic particles"). The (F) binder composed of acrylic particles tends to improve the fixability of the (A) reflecting agent or the (E) coloring material and improve the durability of a printed material. The (F) binder is more preferably composed of a (meth)acrylic resin that does not irritate the skin. The acrylic particles are preferably selected from components described in the list of cosmetic ingredient label names in the Pharmaceutical Affairs Law in Japan, components in accordance with EU cosmetics regulation (Cosmetics Directive 76/768/EEC), and components described in International Cosmetic Ingredient Dictionary and Handbook (Jan. 1, 2002, 9th edition) of the Cosmetic, Toiletry & Fragrance Association (CTFA) in U.S.A. and may be acrylic resin particles used in known cosmetics.

Specific examples of (meth)acrylic resins constituting the acrylic particles include homopolymers of (meth)acrylic monomers, copolymers of two or more (meth)acrylic monomers, and copolymers of (meth)acrylic monomers and other monomers.

Examples of the (meth)acrylic monomers include acrylic acid, methyl acrylate, ethyl acrylate, acrylamide, n-propyl acrylate, n-butyl acrylate, isobutyl acrylate, octyl acrylate, 2-ethylhexyl acrylate, N,N-dimethylaminoethyl acrylate, acrylonitrile, methacrylic acid, ethyl methacrylate, methacrylamide, n-propyl methacrylate, n-butyl methacrylate, isobutyl methacrylate, 2-ethylhexyl methacrylate, octyl methacrylate, hydroxyethyl methacrylate, and N,N-dimethylaminoethyl methacrylate.

Examples of other monomers that can be copolymerized with the (meth)acrylic monomers include styrene, vinyl acetate, silicone macromers, fluorinated monomers, and alkoxy silane unsaturated monomers.

The (F) binder preferably has an average particle size in the range of 30 to 150 nm. The average particle size is the median (D50) of the integrated value of the particle size distribution measured by a laser diffraction method. More preferably, the average particle size (D50) ranges from 30 to 150 nm, and the 90% value (D90) of the integrated value of the particle size distribution is 250 nm or less. The (F) binder with an average particle size in such a range can easily bind the (A) reflecting agent or the (E) coloring material to a substrate.

The amount of the (F) binder is preferably 10 parts or less by mass, more preferably 2.5 to 10 parts by mass, per 100 parts by mass of the cosmetic ink. Although the amount of the (F) binder may be less than 2.5 parts by mass, 2.5 parts or more by mass of the (F) binder can reduce crawling of the cosmetic ink on a substrate. Although an excessively large amount of the (F) binder may result in the cosmetic ink with excessively high viscosity, 10 parts or less by mass of the (F) binder can result in a viscosity suitable for various printing methods.

When the amount of the (A) reflecting agent and the (E) coloring material in the cosmetic ink is 10 parts by mass, the amount of the (F) binder preferably ranges from 0.5 to 10 parts by mass, more preferably 1.5 to 5.7 parts by mass. When the amount of the (A) reflecting agent and the (E) coloring material and the amount of the (F) binder satisfy these ranges, the (A) reflecting agent and the (E) coloring material are more easily fixed to a printed material made from the cosmetic ink. An excessively large amount of the (F) binder, however, may result in the cosmetic ink with excessively high viscosity, as described above.

To prepare the cosmetic ink, in general, the (F) binder dispersed in a dispersion medium (in a slurry or dispersion liquid state) is mixed with the (A) reflecting agent, the (B) higher alcohol, or the (C) purified water. The dispersion medium is also preferably a solvent that does not irritate the skin, such as the above higher alcohol or water.

<Others>

As described above, the cosmetic ink according to the present embodiment may contain the (E) coloring material, a film forming agent, and various additive agents, if necessary.

The (E) coloring material in the cosmetic ink may be of any type but, from the perspective of skin irritancy, is preferably selected from components described in the list of cosmetic ingredient label names in the Pharmaceutical Affairs Law in Japan, components in accordance with EU cosmetics regulation (Cosmetics Directive 76/768/EEC), and components described in International Cosmetic Ingredient Dictionary and Handbook (Jan. 1, 2002, 9th edition) of the Cosmetic, Toiletry & Fragrance Association (CTFA) in U.S.A. The (E) coloring material may be a known inorganic pigment, organic pigment, or dye. The (E) coloring material is selected according to the color and appearance of the cosmetic sheet to be produced. The (E) coloring material includes not only color pigments and color dyes for coloring cosmetic sheets, for example, but also nacreous pigments for making cosmetic sheets glossy. The cosmetic ink may contain one or two or more of the (E) coloring materials. Part of the (A) reflecting agent may function as the (E) coloring material.

Examples of the (E) coloring material include inorganic red pigments, such as iron oxide, iron hydroxide, and iron titanate; inorganic brown pigments, such as γ-iron oxide; inorganic yellow pigments, such as yellow iron oxide and ocher; inorganic black pigments, such as black iron oxide and carbon black; white pigments, such as titanium oxide; inorganic purple pigments, such as manganese violet and cobalt violet; inorganic green pigments, such as chromium hydroxide, chromium oxide, cobalt oxide, and cobalt titanate; inorganic blue pigments, such as Prussian blue (ferric ferrocyanide) and ultramarine blue; lakes made from various tar dyes; lakes made from various natural dyes; and synthetic resin powders produced by combining these powders.

Examples of the nacreous pigments include titanium oxide coated mica, bismuth oxychloride, titanium oxide coated bismuth oxychloride, titanium oxide coated talc, argentine, and titanium oxide coated colored mica.

When the (E) coloring material is composed of a component insoluble in the (B) higher alcohol and the (C) purified water, the (E) coloring material may have any shape, for example, spherical or acicular. The median (D50) of the integrated value of the particle size distribution of the (E) coloring material measured by a laser diffraction method preferably ranges from 125 nm to 2 μm, more preferably 125 to 1000 nm. More preferably, the average particle size (D50) ranges from 125 to 1000 nm, and the 90% value (D90) of the integrated value of the particle size distribution is 3000 nm or less. With the average particle size (D50) of the particle size distribution of the (E) coloring material in the above range, the cosmetic ink can be applied with various printing methods.

The amount of the (E) coloring material is preferably 40 parts or less by mass, more preferably 3 to 10 parts by mass, per 100 parts by mass of the cosmetic ink. 3 parts or more by mass of the (E) coloring material can easily provide a cosmetic sheet with the color or gloss derived from the (E) coloring material. An excessively large amount of the (E) coloring material may make it difficult to apply the cosmetic ink with various printers due to aggregation of the (E) coloring material. As long as the amount of the (E) coloring material is 40% or less by mass, the (E) coloring material rarely aggregates, and the cosmetic ink can be stably applied.

The cosmetic ink according to the present embodiment may contain a film forming agent, if necessary. The film forming agent is a compound that improves the film formation (for example, drying characteristics) of the cosmetic ink. The "film forming agent", as used herein, refers to a compound that can be dispersed in water at room temperature (except the components corresponding to the (F) binder). The cosmetic ink may contain one or two or more film forming agents. The specific type of film forming agent is described in detail in a second embodiment and is not described in detail here.

The amount of the film forming agent is preferably 20 parts or less by mass, more preferably 0.3 to 5 parts by mass, per 100 parts by mass of the cosmetic ink according to the present embodiment. 0.3 parts or more by mass of the film forming agent can improve the drying characteristics of the cosmetic ink, as described in the second embodiment. Although an excessively large amount of the film forming agent may result in the cosmetic ink with excessively high viscosity, 20 parts or less by mass of the film forming agent can result in the cosmetic ink with a viscosity suitable for various printing methods.

The cosmetic ink may further contain various additive agents without compromising the objects and advantages of the present embodiment. Such additive agents are preferably compounds with negative skin irritancy. Examples of the additive agents include surfactants, pH-adjusting agents, thickeners, ultraviolet absorbers, ultraviolet scattering agents, antiseptic antimold agents, deoxidizers, antioxidants, antiseptic agents, antifading agents, antifoaming agents, perfumes, and solvents other than the (B) higher alcohol and the (C) purified water.

The cosmetic ink may contain a water-soluble polymer (a polymer not corresponding to the film forming agent) that binds the (A) reflecting agent or the (E) coloring material to a substrate, without compromising the objects and advantages of the present embodiment.

<Method for Preparing Cosmetic Ink>

The cosmetic ink can be prepared by mixing the (A) reflecting agent, the (B) higher alcohol, the (C) purified water, a slurry or dispersion liquid containing the (F) binder, and other optional components in a dispersing apparatus. The components can be mixed in a dispersing apparatus, such as a known ball mill, sand mill, rolling mill, homomixer, or attritor.

1-2. Second Embodiment

The cosmetic ink according to the second embodiment of the present disclosure contains (B) a higher alcohol having 3 or more carbon atoms, (C) purified water, (D) a film forming agent, and (E) a coloring material.

When a known ink containing a pigment and a solvent (for example, water or a higher alcohol) is applied to a substrate, the solid component of the ink moves slower as the solvent evaporates and is finally fixed to the substrate. Thus, the solvent needs to evaporate almost completely to fix the solid component of the ink to a substrate.

The cosmetic ink according to the present embodiment contains the (D) film forming agent. As described above, the film forming agent is a resin that can be dispersed in water at room temperature and is contained as sol in the cosmetic ink according to the present embodiment. When the cosmetic ink is applied to a substrate, the molecules of the (D) film forming agent come closer to one another as the solvent (the (B) higher alcohol and the (C) purified water) in the coating film evaporates and decreases, and form a hydrogen bond, ionic bond, or hydrophobic bond, thereby forming a cross-linked structure. Consequently, a film is formed within the coating film and restricts the movement of the solid component in the cosmetic ink. Thus, after the application of the cosmetic ink, the solid component of the cosmetic ink is easily fixed to a substrate at an early stage, and this greatly shortens the image fixation (herein also referred to as "drying" for convenience) time.

In addition to these essential components, the cosmetic ink according to the present embodiment may further contain a reflecting agent, a binder, various additive agents, and a water-soluble polymer, if necessary. The (B) higher alcohol, the (C) purified water, the (E) coloring material, the (A) reflecting agent, a binder, various additive agents, and a water-soluble polymer in the cosmetic ink according to the second embodiment may be the same as the compounds in the cosmetic ink according to the first embodiment, and their respective contents may also be the same in the first and second embodiments. These compounds are therefore not described below, and only the (D) film forming agent is described below.

<(D) Film Forming Agent>

The (D) film forming agent used in the cosmetic ink according to the present embodiment is a compound that is soluble in the (B) higher alcohol and/or the (C) purified water and is one or more compounds selected from the group consisting of acrylic polymers, polysaccharide polymers, sugar alcohols, sterols, esters, and modified corn starches. The cosmetic ink may contain one or two or more of the (D) film forming agents. The (D) film forming agent composed of a compound selected from the group can greatly accelerate the drying of a coating film formed of the cosmetic ink.

The (D) film forming agent preferably has an HLB value of 8 or more, more preferably 8 to 19. The (D) film forming agent having an HLB value of 8 or more is easily and homogeneously dissolved in the (B) higher alcohol or the (C) purified water. The HLB value is an index representing the relative affinity ratio for oil and water in an oil-water system. In general, a substance having a higher HLB value has a higher affinity for water. The HLB value in the present specification is determined by the Griffin method.

Preferably, the (D) film forming agent is also a material that does not irritate the skin. Examples of the acrylic polymers include chain acrylic polymers having no ring structure in their molecules, such as alkyl acrylate copolymers, 2-amino-2-methyl-1-propanol salts (hereinafter also referred to as "AMP") of alkyl acrylate copolymers, sodium salts (hereinafter also referred to as "Na") of alkyl acrylate copolymers, alkyl acrylate copolymer ammonium, acrylic acid-alkyl acrylate copolymers, alkyl acrylate-diacetone acrylamide copolymers, alkyl acrylate-diacetone acrylamide copolymer AMPs, 2-amino-2-methyl-1,3-propanediol salts (hereinafter also referred to as "AMPD") of alkyl acrylate-diacetone acrylamide copolymers, hydroxyethyl acrylate-methoxyethyl acrylate copolymers, hydroxyethyl acrylate-butyl acrylate-methoxyethyl acrylate copolymers, acrylates-alkyl acrylate (1 to 18 carbon atoms)-alkyl (1 to 8 carbon atoms) acrylamide copolymer AMPs, alkyl acrylate-octylacrylamide copolymers, acrylates-t-butylacrylamide copolymers, acrylates-ethylhexyl acrylate copolymers, acrylates copolymers, acrylates copolymer AMPs, acrylates copolymers Na, and polyurethane-14-acrylates copolymers AMP; and cyclic acrylic polymers having a ring structure in their molecules, such as styrene-alkyl acrylate copolymers, styrene-acrylates copolymers, styrene-acrylamide copolymers, polyurethane-1 (a compound represented by INCI name: POLYURETHANE-1), polyacrylate-22 (a compound represented by INCI name: POLYACRYLATE-22), tricontanyl polyvinylpyrrolidone (PVP), (eicosene/vinylpyrrolidone) copolymers, (vinylpyrrolidone/hexadecene) copolymers, and vinyl acetate-butyl maleate-isobornyl acrylate copolymers.

Examples of the polysaccharide polymers include gum arabic, glucan, succinoglycan, carrageenan, karaya gum, tragacanth gum, guar gum, locust bean gum, galactomannan gum, xanthan gum, starch, carob gum, quince seed (Cydonia oblonga), casein, dextrin, gelatin, sodium pectate, sodium alginate, methylcellulose, ethylcellulose, carboxymethylcellulose, hydroxyethylcellulose, hydroxypropylcellulose, crystalline cellulose, O-[2-hydroxy-3-(trimethylammonio) propyl]hydroxyethylcellulose chloride, O-[2-hydroxy-3-(trimethylammonio)propyl]guar gum chloride, O-[2-hydroxy-3-(trimethylammonio)propyl]locust bean gum chloride, starch hydroxypropyltrimonium chloride, glyceryl glucoside, glycosyl trehalose, Tremella polysaccharide, and dextrin isostearate.

Examples of the sugar alcohols include sorbitol, maltitol, and glucose. The sterols are compounds having a sterol skeleton. Examples of the sterols include phytosterols, such as campesterol, campestanol, brassicasterol, 22-dehydrocampesterol, stigmasterol, stigmastanol, 22-dihydrospinasterol, 22-dehydrostigmastanol, 7-dehydrostigmasterol, sitosterol, tirucallol, euphol, fucosterol, isofucosterol, codisterol, clionasterol, poriferasterol, clerosterol, 22-dehydroclerosterol, fungisterol, chondrillasterol, avenasterol, vernosterol, and pollinastanol; zoosterols, such as cholesterol, dihydrocholesterol, cholestanol, coprostanol, epicoprosterol, epicoprostanol, 22-dehydrocholesterol, desmosterol, 24-methylenecholesterol, lanosterol, 24,25-dihydrolanosterol, norlanosterol, spinasterol, dihydroagnosterol, agnosterol, lophenol, and lathosterol; mycosterols, such as dehydroergosterol, 22,23-dihydroergosterol, episterol, ascosterol, and fecosterol; and hydrogenated compounds thereof.

Examples of the esters include dipentaerythritol fatty acid esters having a ring structure in their molecules (cyclic ester compounds), such as dipentaerythrityl hexa(hydroxystearate/stearate/rosinate) and dipentaerythrityl (hydroxystearate/stearate/rosinate); dipentaerythritol fatty acid esters having no ring structure in their molecules (chain ester compounds), such as dipentaerythrityl hexahydroxystearate, dipentaerythrityl tetra(hydroxystearate/isostearate), and dipentaerythrityl (hydroxystearate/isostearate); hydrogenated castor oil fatty acid esters (chain ester compounds), such as hydrogenated castor oil stearate, hydrogenated castor oil isostearate, and hydrogenated castor oil hydroxystearate; cholesterol fatty acid esters (cyclic ester compounds), such as cholesteryl hydroxystearate; phytosterol fatty acid esters (cyclic ester compounds), such as phytosteryl oleate and macadamia nut oil fatty acid phytosteryl; hydrogenated vegetable oils (chain ester compounds), such as hydrogenated coconut oil and hydrogenated palm oil; (phytosteryl/isostearyl/cetyl/stearyl/behenyl) dimer dilinoleate (cyclic ester compound); sucrose pentahydroxystearate (cyclic ester compound); and di(octyldodecyl/phytosteryl/behenyl) lauroyl glutamate (cyclic ester compound).

The modified corn starches may be corn starches modified with any compound without compromising the objects and advantages of the present embodiment and may be hydroxypropyl modified starches produced by a reaction between corn starch and 3-(dodecenyl)dihydro 2,5-furandione.

Among these, preferred in terms of improved drying characteristics of the cosmetic ink are acrylates copolymers, acrylates (ethylhexyl acrylate) copolymers, polyurethane-14-acrylates copolymer AMPs, alkyl acrylate copolymer ammonium, dimer dilinoleyl bis(behenyl/isostearyl/phytosteryl) dimer dilinoleate-hydrogenated triglyceryl rosinate, xanthan gum crosspolymer-hydroxyethylcellulose, Tremella polysaccharide, modified corn starches, and dextrin isostearate, and more preferred are acrylates copolymers, acrylates (ethylhexyl acrylate) copolymers, polyurethane-14-acrylates copolymer AMPs, alkyl acrylate copolymer ammonium, dimer dilinoleyl bis(behenyl/isostearyl/phytosteryl) dimer dilinoleate-hydrogenated triglyceryl rosinate, xanthan gum crosspolymer-hydroxyethylcellulose, and Tremella polysaccharide.

The drying time after the application of the cosmetic ink is greatly shortened when the (D) film forming agent contains both a cyclic compound having a ring structure in its molecules and a chain compound having no ring structure in its molecules and the volume fraction of the cyclic compound relative to the total volume of the cyclic compound and the chain compound ranges from 0.01 to 0.66. The volume fraction of the cyclic compound more preferably ranges from 0.1 to 0.6. In the coating film, the chain compound forms a network structure. The ring structures of the cyclic compound are two-dimensionally linked or are stacked (hereinafter also collectively referred to as a "link structure"). When the cyclic compound and the chain compound that satisfy the above volume fraction are contained, the network structure formed by the chain compound and the link structure formed by the cyclic compound are formed in a well-balanced manner, and the film is formed faster than in the case where only one of the structures is contained. In contrast, an excessively high or low volume fraction of the cyclic compound often results in steric hindrance during the formation of the film, and the synergistic effect on the drying of the cosmetic ink may not be produced.

The amount of the (D) film forming agent is preferably 20 parts or less by mass, more preferably 0.3 to 5 parts by mass, per 100 parts by mass of the cosmetic ink. As described above, 0.3 parts or more by mass of the (D) film forming agent can improve the drying characteristics of the cosmetic ink. Although an excessively large amount of the (D) film forming agent may result in the cosmetic ink with excessively high viscosity, 20 parts or less by mass of the film forming agent can result in the cosmetic ink with a viscosity suitable for various printing methods.

To prepare the cosmetic ink, in general, the (D) film forming agent is dissolved in a solvent and is then mixed with the (B) higher alcohol, the (C) purified water, and the (E) coloring material. The solvent is also preferably a solvent that does not irritate the skin, such as the above higher alcohol or water.

<Method for Preparing Cosmetic Ink>

The cosmetic ink according to the present embodiment can be prepared by mixing the (B) higher alcohol, the (C) purified water, the (E) coloring material, a solution containing the (D) film forming agent, and other optional components in a dispersing apparatus. The components can be mixed in a dispersing apparatus, such as a known ball mill, sand mill, rolling mill, homomixer, or attritor.

1-3. Physical Properties of Cosmetic Ink

Both the cosmetic ink according to the first embodiment and the cosmetic ink according to the second embodiment preferably have a viscosity of 50 mPa·s or less, more preferably 1 to 20 mPa·s, still more preferably 3.5 to 8 mPa·s, measured with a cone-plate viscometer at a rate of 1000 (1/s) at 25° C. The cosmetic ink with a viscosity in such a range can be easily applied with various printers. In particular, the cosmetic ink with a viscosity in such a range can be easily and stably ejected from an ink jet apparatus.

The cosmetic ink preferably has a pH in the range of 6 to 10, more preferably 7.5 to 9.5. The cosmetic ink with a pH in such a range does not erode members of various printers, and the coloring material and the reflecting agent rarely aggregate during long-term storage of the cosmetic ink.

The cosmetic ink preferably has a surface tension of 50 mN/m or less, more preferably 32 to 46 mN/m. The surface tension is measured at 25° C. The cosmetic ink with a surface tension of 50 mN/m or less applied to various substrates with various printers has good wettability and can form a film with a uniform thickness. Although the surface tension can be measured by various methods, the above values are measured by the pendant drop method, which is employed in general-purpose apparatuses.

The average particle size of the particles in the cosmetic ink, that is, the median (D50) of the integrated value of the particle size distribution measured by a laser diffraction method preferably ranges from 125 nm to 2 μm. More preferably, the average particle size (D50) ranges from 125 to 1000 nm. Still more preferably, the average particle size (D50) ranges from 125 to 1000 nm, and the 90% value (D90) of the integrated value of the particle size distribution is 3000 nm or less. The cosmetic ink containing particles with an average particle size in such a range can be stably ejected from various printers, particularly ink jet apparatuses. The cosmetic ink with D50 or D90 in such a range can be stably ejected from an ink jet apparatus.

Preferably, the cosmetic ink has negative skin irritancy, that is, is biologically safe. With negative skin irritancy, the cosmetic ink can be used in applications involving contact with the skin. The term "negative skin irritancy", as used herein, refers to cell viability of more than 50% in a test using a three-dimensional skin model, which is an alternative method to the skin irritancy test. In the alternative method to the skin irritancy test, a 5% sodium dodecyl sulfate (SDS) solution is used as an irritancy control, and phosphate-buffered saline (PBS) is used as a negative control. After the ink is exposed to the three-dimensional skin model for 18 hours, cell viability is determined in an MTT test.

In one method of providing the cosmetic ink with negative skin irritancy, all the components in the cosmetic ink are selected from components described in the list of cosmetic ingredient label names in the Pharmaceutical Affairs Law in Japan, components in accordance with EU cosmetics regulation (Cosmetics Directive 76/768/EEC), and components described in International Cosmetic Ingredient Dictionary and Handbook (Jan. 1, 2002, 9th edition) of the Cosmetic, Toiletry & Fragrance Association (CTFA) in U.S.A.

1-4. Ink Cartridge

The cosmetic ink can be stored in a cartridge, for example. The cartridge may be of any type and structure and is selected for each printer for applying the cosmetic ink. One example of the ink cartridge has an ink storage for storing the cosmetic ink and an ink supply port for supplying the ink to a recording head of the printer.

2. Method for Producing Cosmetic Sheet

A cosmetic sheet according to the present disclosure can be produced by a production method that includes the step of applying the cosmetic ink to a substrate and the step of drying the cosmetic ink applied to the substrate.

The cosmetic ink can be applied to a substrate by any method, for example, by a known method. Examples of such an application method include an ink jet printing method, a screen printing method, offset printing, and gravure printing. Among these, the ink jet method is preferred because the cosmetic ink can be applied multiple times depending on the skin conditions and skin color of the user of the cosmetic sheet and can be applied by multilayer printing. A method for producing a cosmetic sheet is described in the following example in which the cosmetic ink is applied by an ink jet method. However, the present disclosure is not limited to this method.

The cosmetic ink can be applied to a substrate by an ink jet method using any ink jet apparatus, for example, of a known piezoelectric system, thermal system, or electrostatic system. Among these, an ink jet apparatus of a piezoelectric device system is preferred because it obviates the need for heating, which is required in a thermal ink jet system.

The cosmetic ink may be applied to a substrate one or two or more times. Cosmetic inks with different compositions (for example, pigments of different types or concentrations) may be filled in ink tanks of an ink jet apparatus and may be successively applied to a substrate from the ink jet apparatus. Cosmetic inks with different compositions may be mixed in an ink jet apparatus to prepare a mixed ink, which is then applied to a substrate. In the case where cosmetic inks are used in combination, at least one of the cosmetic inks is a cosmetic ink according to the present disclosure. Preferably, all the cosmetic inks are cosmetic inks according to the present disclosure in terms of the drying characteristics of the cosmetic inks or the hiding power of the printed material. When the cosmetic ink is applied to a substrate multiple times, the cosmetic ink may be dried each time or after application two or more times. A cosmetic ink according to the present disclosure (particularly the cosmetic ink according to the second embodiment) has good drying characteristics. Thus, the cosmetic ink can be quickly dried even after applied multiple times.

The cosmetic ink may be dried by any method that can remove the (B) higher alcohol and the (C) purified water from the cosmetic ink. For example, the cosmetic ink may be dried at atmospheric pressure and at room temperature, or may be dried by heating to a predetermined temperature and/or may be dried under reduced pressure. For heating, heating to a temperature in the range of, for example, 25° C. to 50° C. is preferred. In such a range, the cosmetic ink can be efficiently dried without deterioration of the substrate or the solid component of the cosmetic ink. The reduced pressure is preferably a decrease in pressure in the range of −0.1 to 0 MPa. Under such a reduced pressure, the ink can be efficiently dried.

The cosmetic ink may be applied to any substrate, for example, a base for use in known cosmetic sheets, without compromising the objects and advantages of the present disclosure. Examples of such a substrate include plain paper, special recording paper, plastics, and cloths. The substrate may be composed of one or two or more layers. Among these, preferred are various sheets made of biocompatible materials directly or indirectly attached to or in close contact with the skin.

Examples of the biocompatible materials include polyesters exemplified by poly(glycolic acid), poly(lactic acid), polycaprolactone, poly(ethylene succinate), poly(ethylene terephthalate), and copolymers thereof; polyethers exemplified by poly(ethylene glycol) and poly(propylene glycol); polyamides exemplified by nylon, poly(glutamic acid), poly(aspartic acid), and salts thereof; polysaccharides exemplified by pullulan, cellulose, starch, chitin, chitosan, alginic acid, hyaluronic acid, and corn starch, and salts thereof; silicones exemplified by acrylic silicone and trimethylsiloxysilicic acid; acrylic acids exemplified by alkyl acrylates, silicone acrylate, acrylamide, and copolymers thereof; poly(vinyl alcohol); polyurethane; polycarbonate; poly(acid anhydride); polyethylene; polypropylene; porous layer coating sheets, and nanofiber sheets. Examples of the sheets made of biocompatible materials include sheets for fixing medical components, sports taping sheets, skin decoration sheets, cosmetic sheets, and surgical antiadhesive materials.

A printed material of a cosmetic ink according to the present disclosure (particularly the cosmetic ink according to the first embodiment) has high hiding power and a low light transmittance. Thus, the printed material even on a transparent or translucent substrate can hide the color of the target (for example, skin) to which the cosmetic sheet is attached. A cosmetic sheet produced from a cosmetic ink according to the present disclosure can have a light transmittance of 70% or less at a wavelength in the range of 380 to 780 nm even on a transparent or translucent substrate.

The substrate may have any thickness selected according to the type and use of the substrate and may be 10 μm or less in thickness. A thinner substrate absorbs less solvent (for example, the (B) higher alcohol or the (C) purified water), and an ink dries more slowly. A cosmetic ink according to the present disclosure (particularly the cosmetic ink according to the second embodiment), however, has good drying characteristics. Thus, for example, even a substrate 3000 nm or less in thickness is printable, and even a thin film 10 to 1000 nm in thickness is also printable.

When an image is formed on such a thin film substrate, the thin film substrate may be placed on a support and, after printing, may be separated from the support. The support may be any support and may be composed of a water-absorbing material. A water-absorbing support can rapidly absorb the (B) higher alcohol and the (C) purified water, thereby enabling only the solid component of the cosmetic ink to be adhered to the surface of the substrate. Thus, the resulting image is unlikely to have blurring and can be a high-resolution image. Examples of the water-absorbing support include bases made of paper, cloths, nonwoven fabrics, fabrics, porous layer coating sheets, nanofiber sheets, water-absorbing polymers, and water-soluble polymers.

EXAMPLES

The present disclosure is described in the following examples. The present disclosure is not limited to these examples.

1. Cosmetic Ink A 1-1. Materials

The following materials were used in the examples and comparative examples. The average particle size of particles is the median (D50) of the integrated value of the particle size distribution measured by a laser diffraction method.

(A) Reflecting agents
Titanium oxide a (average particle size: 950 nm)
Titanium oxide b (average particle size: 120 nm)
(B) Higher alcohols
Glycerin
1,3-propanediol
(C) Purified water
(F) Binder Acrylic polymer particles (average particle size: 50 nm)

1-2. Preparation of Cosmetic Ink

The materials were mixed at the component ratio listed in Table 1 below to prepare a cosmetic ink. Table 1 also lists the physical properties of each cosmetic ink. The viscosity was measured with a cone-plate viscometer at a shear rate of 1000 (1/s) at 25° C. The pH was measured with a pH meter (LAQUAtwin manufactured by Horiba, Ltd.). The surface tension was measured with a contact angle meter (DropMaster DM-501, manufactured by Kyowa Interface Science Co., Ltd.) at 25° C.

TABLE 1

|  | Comparative example A | Example A |
|---|---|---|
| (A) Reflecting agent (titanium oxide) | (titanium oxide b) 10 mass% | (titanium oxide a) 10 mass% |
| (B) Higher alcohol (glycerin/1,3-propanediol) | 10 mass%/10 mass% | |
| (C) Purified water | 67.5 mass% | |
| (F) Binder (acrylic polymer particles) | 2.5 mass% | |
| Viscosity (mPa · s) | 3.1 | 2.9 |
| pH | 8.2 | 8.2 |
| Surface tension (mN/m) | 39.4 | 39.7 |

1-3. Evaluation

Figure 1:
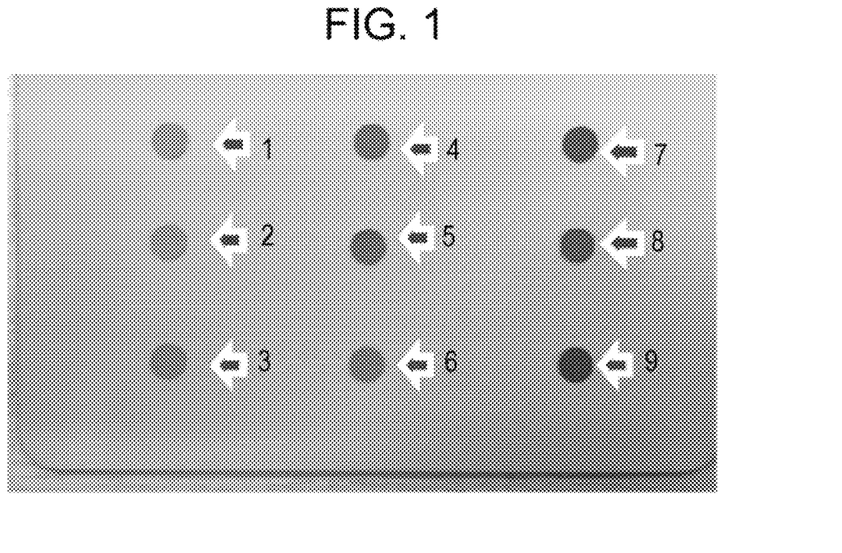
FIG. 1 is a photograph of chloasma models formed on a standard skin model.

As shown in FIG. 1, colored paper sheets (9 types) that imitate chloasma were placed on a standard skin model (Bioskin (manufactured by Beaulax Co., Ltd., product number BIO)) to prepare chloasma models. A cosmetic ink according to Comparative Example A or Example A was applied to an overhead projector (OHP) sheet (light transmittance at a wavelength in the range of 380 to 780 nm: 90%, an A-one OHP film (product number: 27077)) with a squeegee or with an ink jet apparatus to form a solid pattern. The ink jet apparatus was an apparatus equipped with an LB3 ink jet head manufactured by Panasonic Precision Device. After printing, the sheet was dried at 50° C. The coating film formed with the squeegee had an average thickness of 9 μm in Comparative Example A or 10.4 μm in Example A. The coating film formed with the ink jet apparatus had an average thickness of 3.6 μm in Comparative Example A or 2.9 μm in Example A. The coating films formed by each method were placed over chloasma models and were visually rated with respect to transmittance according to the following criteria. Table 2 shows the results. The numbers of the chloasma models in Table 2 correspond to the numbers of the chloasma models in FIG. 1.

○: A chloasma model was not visually recognized.

Δ: Although the color of a chloasma model was recognized, the contour of the chloasma model was not visible.

x: A chloasma model was completely recognized.

TABLE 2

| Application method | Cosmetic ink | Transparency to chloasma model | | | | | | | | |
|---|---|---|---|---|---|---|---|---|---|---|
| | | 1 | 2 | 3 | 4 | 5 | 6 | 7 | 8 | 9 |
| Squeegee | Comparative example A | Δ | Δ | Δ | x | x | x | x | x | x |
| | Example A | ○ | ○ | ○ | ○ | ○ | ○ | ○ | ○ | ○ |
| Ink jet printing | Comparative example A | x | x | x | x | x | x | x | x | x |
| | Example A | ○ | ○ | ○ | ○ | ○ | ○ | ○ | ○ | ○ |

Figure 2:
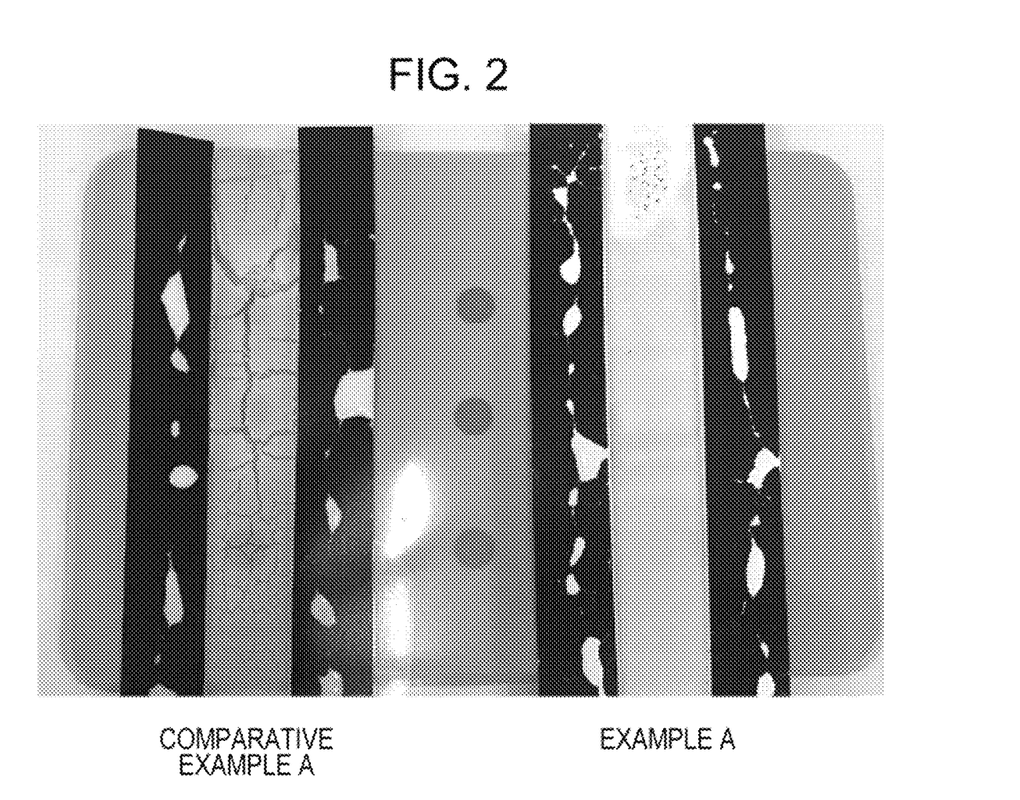
FIG. 2 is a photograph of coating films placed over chloasma models, the coating films being formed of cosmetic inks according to Comparative Example A and Example A using a squeegee.
Figure 3:
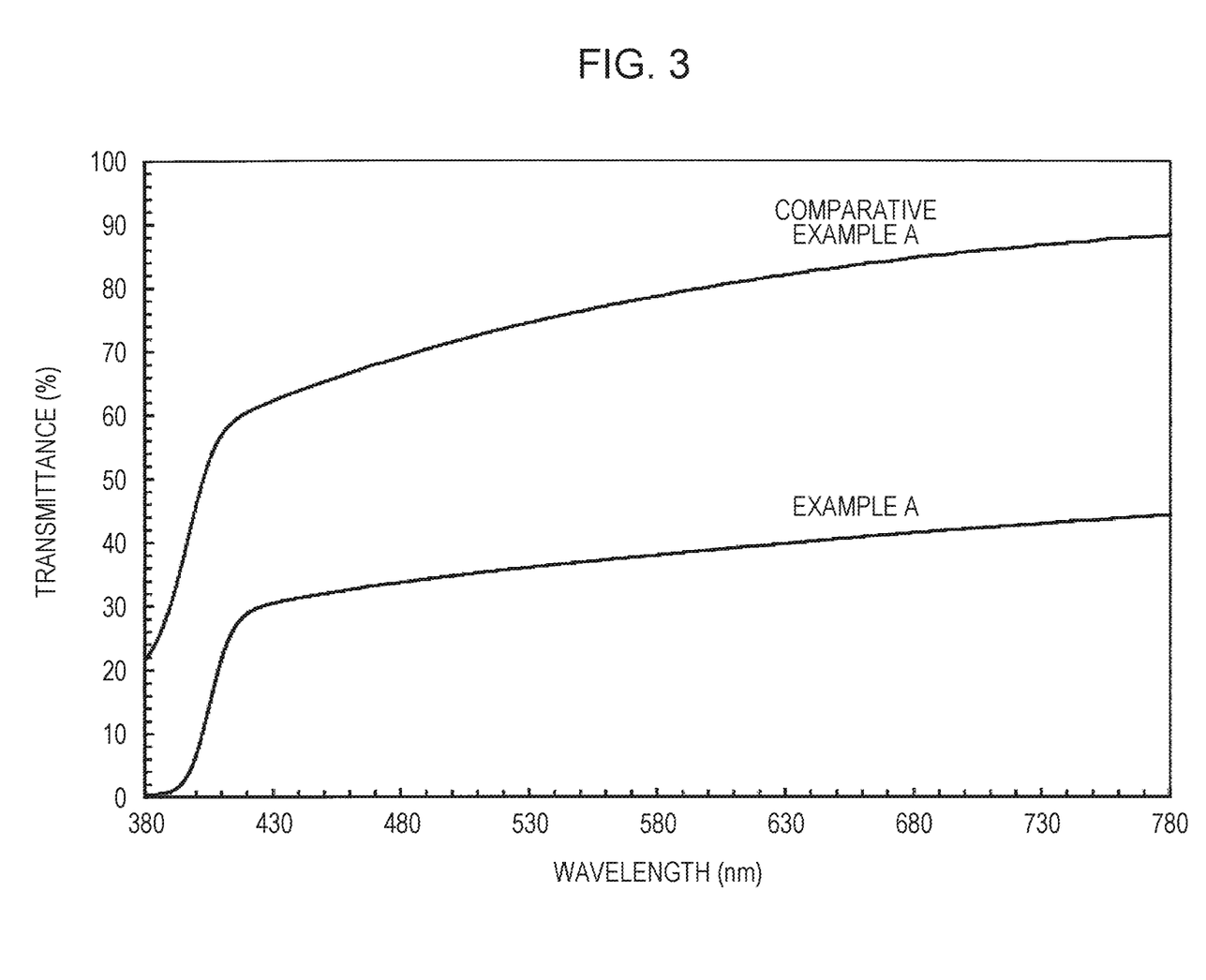
FIG. 3 is a graph of the light transmittance of the coating films at a wavelength in the range of 380 to 780 nm, the coating films being formed of the cosmetic inks according to Comparative Example A and Example A using the squeegee.

FIG. 2 is a photograph of coating films formed with the squeegee placed over chloasma models. In FIG. 2, the coating film of the cosmetic ink according to Comparative Example A was placed over the chloasma models 1 to 3 of FIG. 1, and the coating film of the cosmetic ink according to Example A was placed over the chloasma models 7 to 9 of FIG. 1. FIG. 3 shows the light transmittance of each coating film at a wavelength in the range of 380 to 780 nm. The transmittance of each coating film was measured with ultraviolet-visible-near-infrared spectrophotometer (UV-3600 Plus) manufactured by Shimadzu Corporation.

Figure 4A:
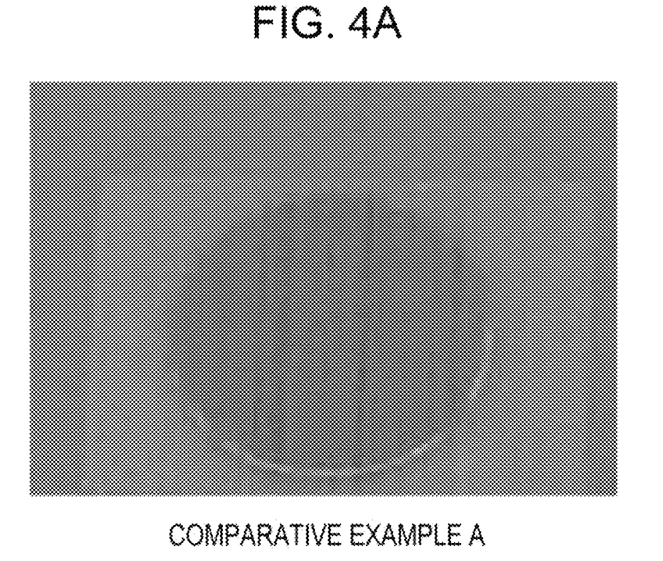
FIG. 4A is a photograph of a coating film placed over a chloasma model, the coating film being formed of the cosmetic ink according to Comparative Example A using an ink jet apparatus.
Figure 4B:
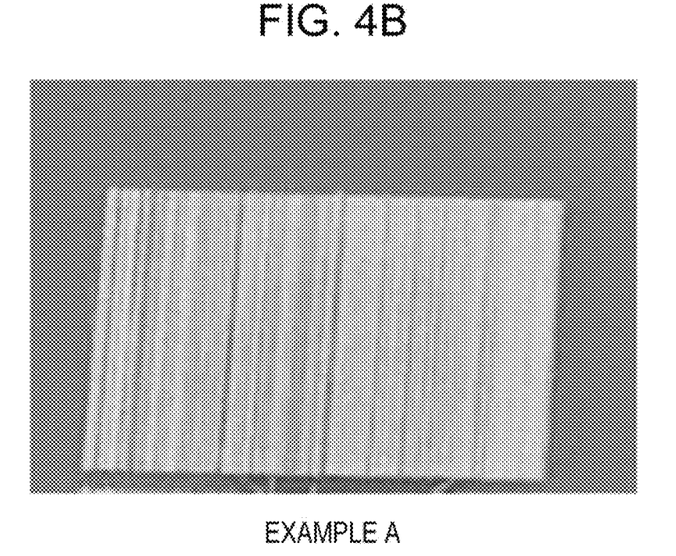
FIG. 4B is a photograph of a coating film placed over a chloasma model, the coating film being formed of the cosmetic ink according to Example A using the ink jet apparatus.
Figure 5:
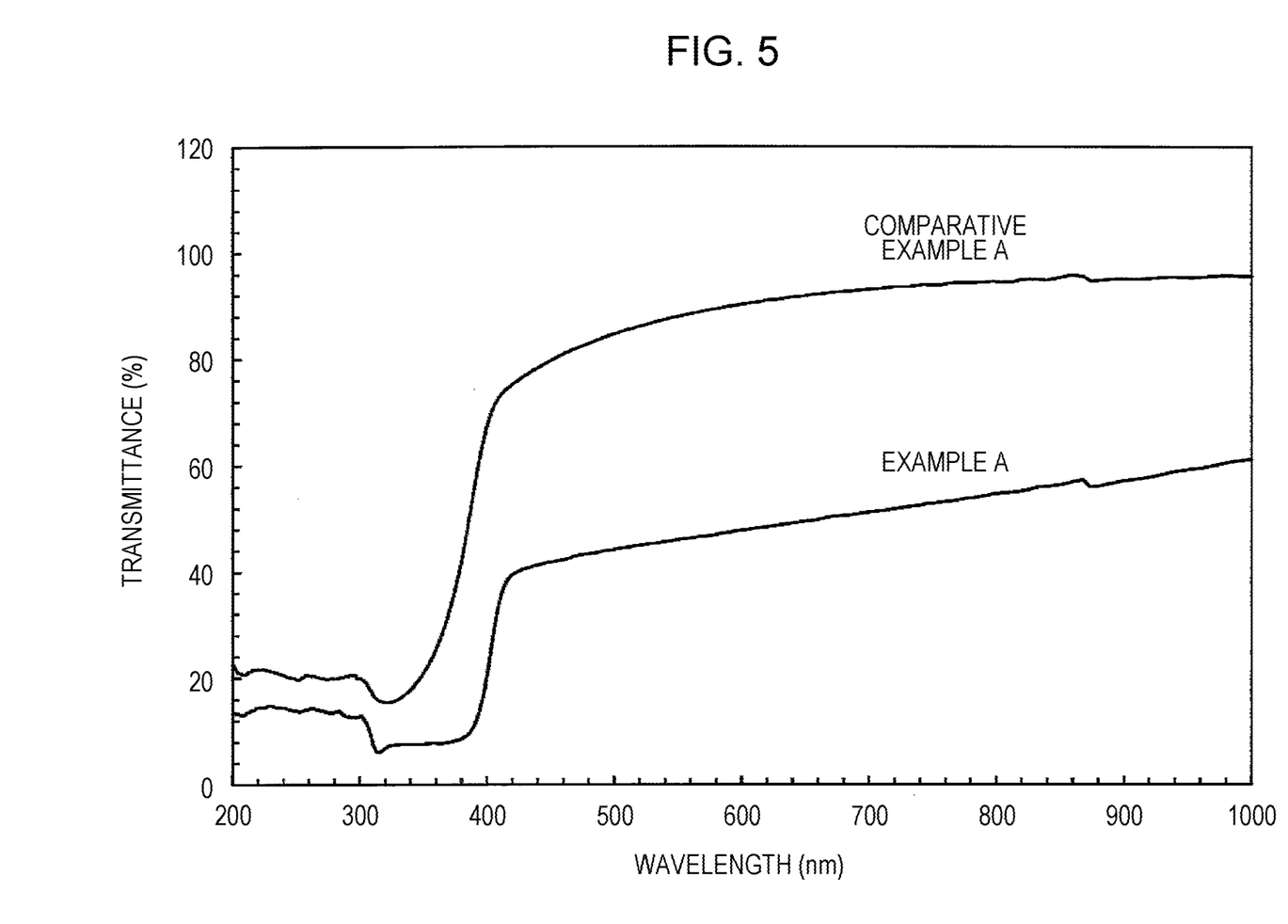
FIG. 5 is a graph of the light transmittance of the coating films at a wavelength in the range of 200 to 1000 nm, the coating films being formed of the cosmetic inks according to Comparative Example A and Example A using the ink jet apparatus.

Likewise, FIGS. 4A and 4B are photographs of the coating films formed with the ink jet apparatus placed over chloasma models. In FIG. 4A, the coating film of the cosmetic ink according to Comparative Example A was placed over the chloasma model 1 of FIG. 1. In FIG. 4B, the coating film of the cosmetic ink according to Example A was placed over the chloasma model 1 of FIG. 1. FIG. 5 shows the light transmittance of each coating film at a wavelength in the range of 200 to 1000 nm.

Table 2 and FIG. 2 show that the coating film of the cosmetic ink containing no reflecting agent according to Comparative Example A formed with the squeegee had insufficient hiding power, though the contours of chloasma models of pale colors were not recognized. Furthermore, chloasma models of deep colors were easily visually recognized. In contrast, the cosmetic ink containing the reflecting agent according to Example A had very good results, and no chloasma model was visually recognized. This is supported by the graph of FIG. 3, in which the coating film of the cosmetic ink according to Example A had lower light transmittance than the coating film of the cosmetic ink according to Comparative Example A in the whole wavelength range.

Table 2 and FIGS. 4A and 4B show that the coating film of the cosmetic ink containing no reflecting agent according to Comparative Example A formed with the ink jet apparatus had insufficient hiding power for any of the chloasma models. In contrast, the cosmetic ink containing the reflecting agent according to Example A had very good results, and no chloasma model was visually recognized. This is supported by the graph of FIG. 5, in which the coating film of the cosmetic ink according to Example A had lower light transmittance than the coating film of the cosmetic ink according to Comparative Example A in the whole wavelength range.

2. Cosmetic Ink B 2-1. Materials

The following materials were used in the examples and comparative examples.

(B) Higher alcohols

Glycerin 1,3-propanediol (C) Purified water (D) Film forming agents (Acrylic polymers)

Acrylates copolymer, HLB value: approximately 8

Acrylates (ethylhexyl acrylate) copolymer, HLB value: approximately 10

Polyurethane-14-acrylates copolymer AMP, HLB value: approximately 13

Alkyl acrylate copolymer ammonium, HLB value: approximately 8

(Esters)

Dimer dilinoleyl bis(behenyl/isostearyl/phytosteryl) dimer dilinoleate-hydrogenated triglyceryl rosinate, HLB value: approximately 8

(Polysaccharide polymer)

Xanthan gum crosspolymer-hydroxyethylcellulose, HLB value: approximately 8

(E) Coloring materials
Iron oxide red (average particle size: 291 nm)
(F) Binder
Acrylic polymer particles (average particle size: 50 nm)

2-2. Preparation of Cosmetic Ink

The materials were mixed at the component ratio listed in Table 3 below to prepare a cosmetic ink. Table 3 also lists the physical properties of each cosmetic ink.

TABLE 3

|  | Comparative example B | Example B-1 | Example B-2 | Example B-3 | Example B-4 | Example B-5 | Example B-6 | Example B-7 |
|---|---|---|---|---|---|---|---|---|
| (B) Higher alcohol (glycerin/1,3-propanediol) | | | | 10 mass %/10 mass % | | | | |
| (C) Purified water | 67.5 mass % | 65.25 mass % | 66.0 mass % | 66.1 mass % | 65.25 mass % | 66.05 mass % | 62.5 mass % | 67.2 mass % |
| (D) Film forming agent | — | 2.25 mass %*1 | 1.5 mass %*2 | 1.4 mass %*3 | 2.25 mass %*4 | 1.45 mass %*4 | 5 mass %*5 | 0.3 mass %*6 |
| (E) Coloring material (iron oxide red) | | | | 10 mass % | | | | |
| (F) Binder (acrylic polymer particles) | | | | 2.5 mass % | | | | |
| Viscosity (mPa · s) | 5.6 | 4.5 | 5.0 | 6.0 | 4.4 | 4.8 | 4.7 | 25.5 |
| pH | 8.3 | 8.3 | 8.3 | 8.3 | 8.3 | 8.3 | 8.3 | 8.3 |
| Surface tension (mN/m) | 37.5 | 38.5 | 36.3 | 35.3 | 37.4 | 37.7 | 37.9 | 33.1 |

2-3. Evaluation (Evaluation in Squeegee Coating Film)

Each of the cosmetic inks prepared in Examples B-1 to B-7 and Comparative Example B was applied to an ink jet recording paper sheet (thickness: 270 μm) with a squeegee to form a 15 mm×15 mm rectangular solid pattern.

The solid pattern was dried at 50° C. 0.5, 1, 2, 3, and 5 minutes after the formation of the coating film, tissue paper was pressed against the coating film, and the drying characteristics of the ink were rated in terms of the adhesion of the ink. The ratings were based on the following criteria. Table 4 shows the results.

◯: No ink adhesion.
▲: Almost no ink adhered, but the ink after hardening became sticky and adhered partly.
Δ: The ink adhered (slightly), but the adhered ink was liquid and permeated into the tissue paper.
x: The ink adhered (markedly), and the adhered ink was liquid and permeated into the tissue paper.

drying characteristics than the cosmetic ink containing no film forming agent according to Comparative Example B. In particular, Example B-7 had very good results, in which the ink was almost dried after 1 minute.

(Evaluation of Ink Jet Coating Film)

Each of the cosmetic inks prepared in Examples B-1 to B-5 and B-7 and Comparative Example B was charged into an ink tank of an ink jet apparatus equipped with an LB3 ink jet head manufactured by Panasonic Precision Device. A poly(lactic acid) sheet 200 nm in thickness was put on a filter paper support to prepare a substrate. The cosmetic ink was applied to the poly(lactic acid) sheet with the ink jet apparatus to form a 15 mm×15 mm rectangular solid pattern. The ink was further applied in the same pattern four times to prepare a 5-layer coating film.

The solid pattern was dried at 40° C. and at −0.1 MPa. Immediately (0), 15, 30, 45, and 60 minutes after the formation of the coating film, tissue paper was pressed against the coating film, and the drying characteristics of the ink were rated in terms of the adhesion of the ink. The ratings were based on the following criteria. Table 5 shows the results.

◯: No ink adhesion.
Δ: The ink adhered (slightly), but the adhered ink was liquid and permeated into the tissue paper.
x: The ink adhered (markedly), and the adhered ink was liquid and permeated into the tissue paper.

TABLE 4

|  | After 0.5 min | After 1 min | After 2 min | After 3 min | After 5 min |
|---|---|---|---|---|---|
| Comparative example B | x | x | Δ | ◯ | ◯ |
| Example B-1 | x | Δ | ◯ | ◯ | ◯ |
| Example B-2 | x | x | ◯ | ◯ | ◯ |
| Example B-3 | x | Δ | ▲ | ◯ | ◯ |
| Example B-4 | x | Δ | ◯ | ◯ | ◯ |
| Example B-5 | x | x | ◯ | ◯ | ◯ |
| Example B-6 | x | x | ◯ | ◯ | ◯ |
| Example B-7 | Δ | ◯ | ◯ | ◯ | ◯ |

Table 4 shows that the cosmetic inks containing the film forming agent according to Examples B-1 to B-7 had better

TABLE 5

|  | After 0 min | After 15 min | After 30 min | After 45 min | After 60 min |
|---|---|---|---|---|---|
| Comparative example B | x | x | x | x | ◯ |
| Example B-1 | x | ◯ | ◯ | ◯ | ◯ |
| Example B-2 | x | x | ◯ | ◯ | ◯ |
| Example B-3 | x | ◯ | ◯ | ◯ | ◯ |
| Example B-4 | x | ◯ | ◯ | ◯ | ◯ |
| Example B-5 | x | ◯ | ◯ | ◯ | ◯ |
| Example B-7 | x | ◯ | ◯ | ◯ | ◯ |

Table 5 shows that Comparative Example B containing no film forming agent took approximately 60 minutes to dry, whereas the cosmetic inks containing the film forming agent according to Examples B-1 to B-5 and B-7 took 30 minutes or less to harden. Thus, the film forming agent significantly improved the drying characteristics of the inks.

3. Cosmetic Ink C 3-1. Preparation of Cosmetic Ink

Example B-4 and Example B-7 were mixed together to prepare the cosmetic inks according to Examples C-1 to C-3. The mixing ratio of the inks was controlled such that the (D) film forming agent composed of a chain compound (from Example B-4) and the (D) film forming agent composed of a cyclic compound (from Example B-7) in each cosmetic ink satisfy the volume ratio listed in the following table and such that the amount of the (D) film forming agent in each cosmetic ink was 5% by mass.

TABLE 6

|  | Example B-4 | Example C-1 | Example C-2 | Example C-3 | Example B-7 |
|---|---|---|---|---|---|
| (D) Film forming agent composed of chain compound | 1.0 | 0.67 | 0.5 | 0.33 | — |
| (D) Film forming agent composed of cyclic compound | — | 0.33 | 0.5 | 0.67 | 1.0 |

3-2. Evaluation

Each of the cosmetic inks prepared in Examples B-4 and B-7 and Examples C-1 to C-3 was applied to an ink jet recording paper sheet (thickness: 270 μm) with a squeegee to form a 15 mm×15 mm rectangular solid pattern.

Figure 6:
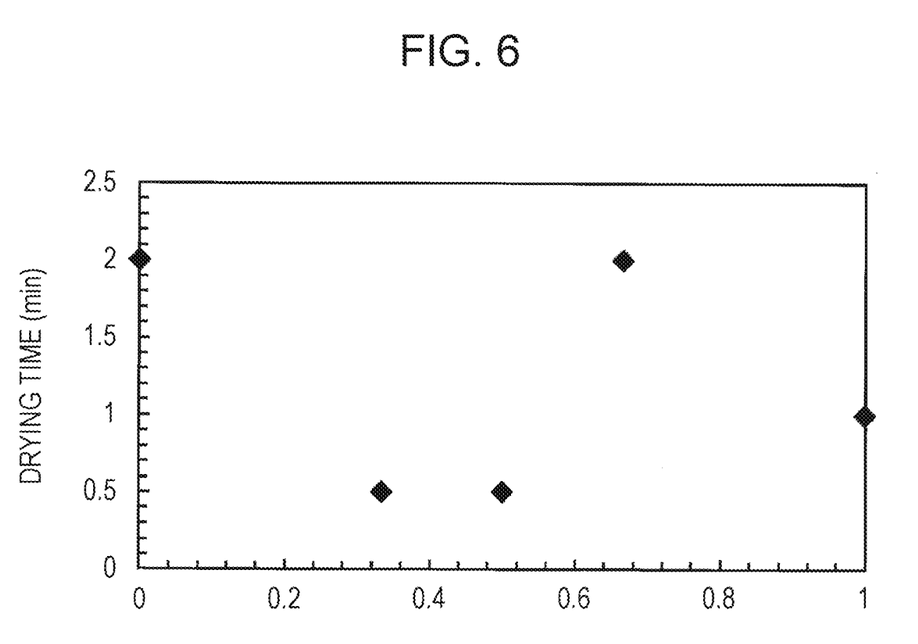
FIG. 6 is a graph of the relationship between the drying time of a cosmetic ink and the volume fraction of a cyclic compound relative to the total volume of (D) a film forming agent (a chain compound and the cyclic compound) in the cosmetic ink.

The solid pattern was dried at 50° C. 0.5, 1, 2, 3, and 5 minutes after the formation of the coating film, tissue paper was pressed against the coating film, and the drying characteristics of the ink were rated in terms of the adhesion of the ink. The ratings were based on the following criteria. Table 7 shows the results. FIG. 6 is a graph of the relationship between the drying time of the cosmetic ink (time to the rating ◯) and the volume fraction of the cyclic compound relative to the total volume of the (D) film forming agent (the chain compound and the cyclic compound).

◯: No ink adhesion.

▲: Almost no ink adhered, but the ink after hardening became sticky and adhered partly.

Δ: The ink adhered (slightly), but the adhered ink was liquid and permeated into the tissue paper.

x: The ink adhered (markedly), and the adhered ink was liquid and permeated into the tissue paper.

TABLE 7

|  | After 0.5 min | After 1 min | After 2 min | After 3 min | After 5 min |
|---|---|---|---|---|---|
| Example B-4 | x | Δ | ◯ | ◯ | ◯ |
| Example C-1 | ◯ | ◯ | ◯ | ◯ | ◯ |
| Example C-2 | ◯ | ◯ | ◯ | ◯ | ◯ |
| Example C-3 | x | Δ | ◯ | ◯ | ◯ |
| Example B-7 | Δ | ◯ | ◯ | ◯ | ◯ |

Table 7 and FIG. 6 show that the volume fraction of the cyclic compound relative to the total volume of the (D) film forming agent (the total volume of the chain compound and the cyclic compound) in the range of 0.01 to 0.66 (Examples C-1 and C-2) resulted in much shorter drying times than in the case of the (D) film forming agent composed of the cyclic compound alone (Example B-7) or the (D) film forming agent composed of the chain compound alone (Example B-4). Even when the (D) film forming agent contained the chain compound and the cyclic compound, the volume fraction of the cyclic compound relative to the total volume of the chain compound and the cyclic compound exceeding 0.66 (Example C-3) resulted in almost the same drying time as in the case of the (D) film forming agent composed of the chain compound alone (Example B-4). It is surmised that the chain compound and the cyclic compound had steric hindrance when forming a network structure and a link structure, respectively.

A cosmetic ink according to an embodiment of the present disclosure has high hiding power when forming a coating film on a light-transmitting film. A cosmetic ink according to another embodiment of the present disclosure has good drying characteristics. Thus, these inks can be applied with high resolution to not only plain paper but also substrates other than paper, such as special recording paper, plastics, and cloths, and are very useful in producing various cosmetic sheets.

What is claimed is:

1. A cosmetic ink comprising:
    (A) a reflecting agent with an average particle size in the range of 125 nm to 2 μm, a 90% value (D90) of an integrated value of a particle size distribution of the reflecting agent being 3000 nm or less;
    (B) a higher alcohol having 3 or more carbon atoms;
    (C) purified water; and
    (F) a binder, wherein the average particle size (D50) of the binder is in the range of 30 to 150 nm,
    wherein the (A) reflecting agent includes white pigments, white extender powders, photoluminescent powders, organic low-molecular-weight powders, natural organic powders, metal powders, or composite powders.

2. The cosmetic ink according to claim 1, further comprising
    (E) a coloring material.

3. The cosmetic ink according to claim 2, wherein the (E) coloring material has an average particle size in the range of 125 nm to 2 μm.

4. The cosmetic ink according to claim 1, wherein the cosmetic ink has a viscosity of 50 mPa·s or less measured with a cone-plate viscometer at a shear rate of 1000 (1/s) at 25° C.

5. The cosmetic ink according to claim 1, wherein the cosmetic ink has a pH in the range of 6 to 10.

6. The cosmetic ink according to claim 1, wherein the cosmetic ink has a surface tension of 50 mN/m or less.

7. A ink jet printing ink comprising the cosmetic ink according to claim 1.

8. An ink cartridge comprising the cosmetic ink according to claim 1.

9. A method for producing a cosmetic sheet, comprising:
    applying the cosmetic ink according to claim 1 to a substrate by an ink jet method; and
    drying the cosmetic ink applied to the substrate.

10. The method for producing a cosmetic sheet according to claim 9, wherein the substrate has a thickness of 10 μm or less.

11. The method for producing a cosmetic sheet according to claim 9, wherein the cosmetic sheet has a light transmittance of 70% or less at a wavelength in the range of 380 to 780 nm.

12. A method for producing a cosmetic sheet, comprising:
mixing a plurality of inks of different compositions to prepare a mixed ink;
applying the mixed ink to a substrate; and
drying the mixed ink applied to the substrate,
wherein at least one ink of the plurality of inks is the cosmetic ink according to claim 1.

13. A method for producing a cosmetic sheet, comprising:
successively applying a plurality of inks of different compositions to a substrate; and
drying the inks applied to the substrate,
wherein at least one ink of the plurality of inks is the cosmetic ink according to claim 1.

14. A cosmetic sheet comprising:
a sheet; and
a film of a solidified product of the cosmetic ink according to claim 1 formed on the sheet.

15. The cosmetic ink according to claim 1, wherein the reflecting agent (A) is a white pigment selected from the group consisting of titanium oxide, zinc oxide, cerium oxide, and barium sulfate.

16. The cosmetic ink according to claim 1, wherein the reflecting agent (A) is a white extender powder selected from the group consisting of bentonite, silicic anhydride, aluminum oxide, magnesium oxide, aluminum silicate, aluminum magnesium metasilicate, calcium silicate, barium silicate, and magnesium silicate.

17. The cosmetic ink according to claim 1, wherein the reflecting agent (A) is a photoluminescent powder selected from the group consisting of calcium aluminum borosilicate, and titanium dioxide coated mica.

18. The cosmetic ink according to claim 1, wherein the reflecting agent (A) is a natural organic powder selected from the group consisting of silk powders and cellulose powders.

19. The cosmetic ink according to claim 1, wherein the reflecting agent (A) is a metal powder selected from the group consisting of aluminum powders, gold powders, and silver powders.

20. The cosmetic ink according to claim 1, wherein the amount of the (A) reflecting agent ranges from
more than 10 parts by mass per 100 parts by mass of the cosmetic ink to
less than or equal to 30 parts by mass per 100 parts by mass of the cosmetic ink.

21. The cosmetic ink according to claim 1, wherein
the cosmetic ink further comprises a film forming agent, and
the cosmetic ink has a light transmittance of 70% or less over the entire wavelength range of 380 nm to 780 nm.

* * * * *